US008357813B2

(12) United States Patent
Gerdes et al.

(10) Patent No.: US 8,357,813 B2
(45) Date of Patent: Jan. 22, 2013

(54) PROCESS FOR THE PRODUCTION OF AN OLEFIN OXIDE

(75) Inventors: William Herman Gerdes, Hudson, OH (US); John Robert Lockemeyer, Sugar Land, TX (US); Donald James Remus, Stow, OH (US); Thomas Szymanski, Hudson, OH (US); Randall Clayton Yeates, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/300,112

(22) Filed: Nov. 18, 2011

(65) Prior Publication Data

US 2012/0136166 A1  May 31, 2012

Related U.S. Application Data

(62) Division of application No. 11/921,610, filed as application No. PCT/US2006/021903 on Jun. 6, 2006, now Pat. No. 8,084,390.

(60) Provisional application No. 60/688,245, filed on Jun. 7, 2005.

(51) Int. Cl.
*C07D 301/03* (2006.01)
*C07D 301/10* (2006.01)
*C07D 317/44* (2006.01)
*C07C 27/00* (2006.01)
*C07C 29/00* (2006.01)
*C07C 29/03* (2006.01)
*C07C 31/18* (2006.01)
*C07C 41/00* (2006.01)
*C07C 43/00* (2006.01)
*B01J 23/48* (2006.01)
*B01J 23/50* (2006.01)

(52) U.S. Cl. ....... 549/534; 549/436; 549/536; 549/537; 564/477; 564/487; 568/679; 568/680; 568/860; 568/867; 502/347; 502/348

(58) Field of Classification Search .............. 502/347, 502/348; 549/436, 534, 536, 537; 564/477, 564/487; 568/679, 680, 860, 867
See application file for complete search history.

(56) References Cited

U.S. PATENT DOCUMENTS

| | | | | |
|---|---|---|---|---|
| 2,069,060 A | 1/1937 | Fessler | | 23/142 |
| 3,664,970 A | 5/1972 | De Maio | | 252/454 |
| 4,007,135 A * | 2/1977 | Hayden et al. | | 502/317 |
| 4,171,288 A | 10/1979 | Keith et al. | | 252/462 |
| 4,364,844 A | 12/1982 | Umemura et al. | | 252/435 |
| 4,428,863 A | 1/1984 | Fry | | 502/8 |
| 4,532,231 A | 7/1985 | Johnson | | 502/347 |
| 4,551,443 A | 11/1985 | Hudson | | 502/313 |
| 4,577,047 A | 3/1986 | Hudson | | 585/260 |
| 4,690,913 A | 9/1987 | Nojiri et al. | | 502/340 |
| 4,761,394 A | 8/1988 | Lauritzen | | 502/348 |
| 4,766,105 A | 8/1988 | Lauritzen | | 502/216 |
| 4,774,222 A | 9/1988 | Rashkin | | 502/347 |
| 4,812,437 A | 3/1989 | Nojiri et al. | | 502/243 |
| 4,822,900 A | 4/1989 | Hayden | | 549/534 |
| 4,837,347 A | 6/1989 | Rashkin | | 549/534 |
| 4,845,296 A * | 7/1989 | Ahmed et al. | | 564/477 |
| 4,908,343 A | 3/1990 | Bhasin | | 502/218 |
| 4,916,243 A | 4/1990 | Bhasin et al. | | 549/534 |
| 4,939,114 A | 7/1990 | Nojiri et al. | | 502/348 |
| 5,011,807 A | 4/1991 | Hayden et al. | | 502/218 |
| 5,051,395 A | 9/1991 | Mitchell et al. | | 502/348 |
| 5,057,481 A | 10/1991 | Bhasin | | 502/208 |
| 5,063,195 A | 11/1991 | Jin et al. | | 502/341 |
| 5,081,096 A | 1/1992 | Monnier et al. | | 502/348 |
| 5,100,859 A | 3/1992 | Gerdes et al. | | 502/439 |
| 5,102,848 A | 4/1992 | Soo et al. | | 502/218 |
| 5,112,795 A | 5/1992 | Minahan et al. | | 502/324 |
| 5,145,824 A | 9/1992 | Buffum et al. | | 502/216 |
| 5,173,469 A | 12/1992 | Wunde et al. | | 502/340 |
| 5,187,140 A | 2/1993 | Thorsteinson et al. | | 502/348 |
| 5,281,728 A | 1/1994 | Wunde et al. | | 549/537 |
| 5,380,697 A | 1/1995 | Matusz et al. | | 502/348 |
| 5,384,302 A | 1/1995 | Gerdes et al. | | 502/439 |
| 5,395,812 A | 3/1995 | Nagase et al. | | 502/238 |
| 5,502,020 A | 3/1996 | Iwakura et al. | | 502/317 |
| 5,504,053 A | 4/1996 | Chou et al. | | 502/348 |
| 5,512,530 A | 4/1996 | Gerdes et al. | | 502/351 |
| 5,733,842 A | 3/1998 | Gerdes et al. | | 502/439 |
| 5,739,075 A | 4/1998 | Matusz | | 502/302 |
| 5,801,259 A | 9/1998 | Kowaleski | | 549/536 |
| 5,929,259 A | 7/1999 | Lockemeyer | | 549/534 |

(Continued)

FOREIGN PATENT DOCUMENTS

| | | |
|---|---|---|
| CN | 1049653 | 3/1991 |
| CN | 1106377 A | 5/1995 |

(Continued)

OTHER PUBLICATIONS

Wang:, F.Y.: "Treatise on Materials Science and Technology", vol. 9, NY, pp. 79-81, 1976.

(Continued)

*Primary Examiner* — Patricia L Hailey

(57) ABSTRACT

The invention provides a process for the epoxidation of an olefin, which process comprises reacting a feed comprising an olefin and oxygen in the presence of a catalyst comprising a carrier and silver deposited on the carrier, which carrier comprises at least 85 weight percent α-alumina and has a surface area of at least 1.3 m²/g, a median pore diameter of more than 0.8 μm, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

28 Claims, No Drawings

U.S. PATENT DOCUMENTS

| | | | | |
|---|---|---|---|---|
| 5,935,897 | A | 8/1999 | Trubenbach et al. | 502/527.14 |
| 5,935,898 | A | 8/1999 | Trubenbach et al. | 502/527.14 |
| 6,087,299 | A | 7/2000 | Grub et al. | 502/347 |
| 6,103,916 | A | 8/2000 | Takada et al. | 549/534 |
| 6,114,553 | A | 9/2000 | Kiriki et al. | 549/534 |
| 6,153,556 | A | 11/2000 | Shima et al. | 502/348 |
| 6,281,370 | B1 | 8/2001 | Shima et al. | 549/536 |
| 6,313,325 | B1 | 11/2001 | Shima et al. | 549/534 |
| 6,368,998 | B1 | 4/2002 | Lockemeyer | 502/347 |
| 6,498,122 | B2 | 12/2002 | Nakashiro | 502/347 |
| 6,511,938 | B1 | 1/2003 | Liu et al. | 502/347 |
| 6,579,825 | B2 | 6/2003 | Lockemeyer | 502/347 |
| 6,656,874 | B2 | 12/2003 | Lockemeyer | 502/347 |
| 6,750,173 | B2 | 6/2004 | Rizkalla et al. | 502/348 |
| 6,787,656 | B2 | 9/2004 | Shima et al. | 549/534 |
| 6,831,037 | B2 | 12/2004 | Szymanski et al. | 502/355 |
| 7,507,844 | B2 * | 3/2009 | Pak | 549/534 |
| 7,713,903 | B2 * | 5/2010 | Lockemeyer et al. | 502/202 |
| 7,825,062 | B2 * | 11/2010 | Gerdes et al. | 502/263 |
| 8,084,390 | B2 * | 12/2011 | Gerdes et al. | 502/347 |
| 8,084,632 | B2 * | 12/2011 | Liu et al. | 549/523 |
| 2002/0010094 | A1 | 1/2002 | Lockemeyer | 502/439 |
| 2003/0092922 | A1 | 5/2003 | Shima et al. | 549/534 |
| 2003/0162655 | A1 | 8/2003 | Szymanski et al. | 502/243 |
| 2003/0162984 | A1 | 8/2003 | Lockemeyer et al. | 549/534 |
| 2006/0047130 | A1 | 3/2006 | Yeates et al. | 549/534 |
| 2006/0258532 | A1 | 11/2006 | Thorsteinson et al. | 502/347 |
| 2006/0281631 | A1 | 12/2006 | Gerdes et al. | 502/263 |
| 2007/0185339 | A1 * | 8/2007 | Lu | 549/534 |

FOREIGN PATENT DOCUMENTS

| | | |
|---|---|---|
| CN | 1101272 | 5/1999 |
| CN | 1101272 | 2/2003 |
| CN | 1437590 | 8/2003 |
| EP | 003642 | 8/1979 |
| EP | 076504 | 4/1983 |
| EP | 179584 | 4/1986 |
| EP | 266015 | 5/1988 |
| EP | 327356 | 8/1989 |
| EP | 393785 | 10/1990 |
| EP | 480538 | 4/1992 |
| EP | 496386 | 7/1992 |
| EP | 496470 | 7/1992 |
| EP | 0558346 | 9/1995 |
| EP | 0923986 | 6/1999 |
| EP | 927575 | 7/1999 |
| EP | 0937498 | 8/1999 |
| EP | 1002575 | 5/2000 |
| EP | 1086743 | 3/2001 |
| JP | 63126552 | 5/1988 |
| JP | 5329368 | 12/1993 |
| JP | 11-240777 | 9/1999 |
| JP | 2000-044331 | 2/2000 |
| JP | 2001157839 | 6/2001 |
| JP | 200347851 | 2/2003 |
| WO | WO9501837 | 1/1995 |
| WO | WO9604989 | 2/1996 |
| WO | WO9740932 | 11/1997 |
| WO | WO9740933 | 11/1997 |
| WO | WO9746317 | 12/1997 |
| WO | WO0001535 | 1/2000 |
| WO | WO0015333 | 3/2000 |
| WO | WO0015334 | 3/2000 |
| WO | WO0015335 | 3/2000 |
| WO | WO03072244 | 9/2003 |
| WO | WO03072246 | 9/2003 |
| WO | WO2005023418 | 3/2005 |

OTHER PUBLICATIONS

Reed, J.S.: "Introduction to the Principles of Ceramic Processing", NY, 1988, pp. 152-153, 172-173.

Kirk-Othmer "Encyclopedia of Chemical Technology", 4th Edition, vol. 5, p. 610.

Kirk-Othmer "Encyclopedia of Chemical Technology", 3rd Edition, vol. 9, pp. 445-447.

Brunauer, S., et al.: Adsorption of Gases in Multimolecular Layers, Jrnl. of the American Chemical Society 60, 1938, pp. 309-319.

* cited by examiner

US 8,357,813 B2

PROCESS FOR THE PRODUCTION OF AN OLEFIN OXIDE

CROSS REFERENCE TO RELATED APPLICATIONS

This application is a divisional of U.S. application Ser. No. 11/921,610 filed Dec. 5, 2007, and claims the benefit of International Application No. PCT/US2006/021903, filed Jun. 6, 2006, which designated the U.S. and which claims priority to U.S. Patent Application No. 60/688,245, filed Jun. 7, 2005, with the U.S. Patent and Trademark Office. The entire disclosures of these applications are hereby incorporated by reference.

FIELD OF THE INVENTION

The present invention relates to a catalyst, a process for preparing the catalyst, and a process for the production of an olefin oxide, a 1,2-diol, a 1,2-diol ether, or an alkanolamine.

BACKGROUND OF THE INVENTION

In olefin epoxidation, a feed containing an olefin and an oxygen source is contacted with a catalyst under epoxidation conditions. The olefin is reacted with oxygen to form an olefin oxide. A product mix results that contains olefin oxide and typically unreacted feed and combustion products.

The olefin oxide may be reacted with water to form a 1,2-diol, with an alcohol to form a 1,2-diol ether, or with an amine to form an alkanolamine. Thus, 1,2-diols, 1,2-diol ethers, and alkanolamines may be produced in a multi-step process initially comprising olefin epoxidation and then the conversion of the formed olefin oxide with water, an alcohol, or an amine.

Olefin epoxidation catalysts comprise a silver component, usually with one or more additional elements deposited therewith, on a carrier. Carriers are typically formed of a refractory material, such as alpha-alumina. In general, higher purity alpha-alumina has been found to correlate with better performance. It has also been found for example that the presence of minor amounts of impurities in the carrier such as alkali and/or alkaline earth metals and some forms of silica can have a beneficial effect.

Intuitively it might also be considered that the higher the surface area of the carrier, the greater the area available for deposition of the silver and therefore the more effective the silver deposited thereon. However, this is generally found not to be the case and in modern catalysts the tendency is to use a carrier with a relatively low surface area, for example a surface area of less than 1.3 $m^2/g$, or even less than 1 $m^2/g$.

US 2003/0162984 A1 discloses carriers which have a surface area of at least 1 $m^2/g$. The working examples given show improved initial selectivity and activity of epoxidation catalysts based on carriers having at least 70% of the total pore volume represented by pores with diameters in the range of from 0.2 to 10 μm.

The catalyst performance may be assessed on the basis of selectivity, activity and stability of operation. The selectivity is the fraction of the converted olefin yielding the desired olefin oxide. As the catalyst ages, the fraction of the olefin converted normally decreases with time and to maintain a constant level of olefin oxide production the temperature of the reaction is increased. However this adversely affects the selectivity of the conversion to the desired olefin oxide. In addition, the equipment used can tolerate temperatures only up to a certain level so that it is necessary to terminate the reaction when the reaction temperature would reach a level inappropriate for the reactor. Thus the longer the selectivity can be maintained at a high level and the epoxidation can be performed at an acceptably low temperature, the longer the catalyst charge can be kept in the reactor and the more product is obtained. Quite modest improvements in the maintenance of selectivity over long periods yields huge dividends in terms of process efficiency.

SUMMARY OF THE INVENTION

The present invention provides a catalyst which comprises a carrier and silver deposited on the carrier, which carrier has a surface area of at least 1 $m^2/g$, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

The invention also provides a process for the preparation of a catalyst which process comprises:
a) selecting a carrier which has a surface area of at least 1 $m^2/g$, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm, and
b) depositing silver on the carrier.

The invention also provides a process for the preparation of a catalyst which process comprises depositing silver on a carrier, wherein the carrier has been obtained by a method which comprises forming a mixture comprising:
a) from 50 to 95 weight percent of a first particulate α-alumina having a median particle size ($d_{50}$) of from 5 to 100 μm;
b) from 5 to 50 weight percent of a second particulate α-alumina having a $d_{50}$ which is less than the $d_{50}$ of the first particulate α-alumina and which is in the range of from 1 to 10 μm; and
c) an alkaline earth metal silicate bond material;
weight percent being based on the total weight of α-alumina in the mixture; and firing the mixture to form the carrier.

Further, the invention provides a process for the epoxidation of an olefin, which process comprises reacting a feed comprising an olefin and oxygen in the presence of a catalyst which comprises a carrier and silver deposited on the carrier, which carrier has a surface area of at least 1 $m^2/g$, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

The invention also provides a process for the epoxidation of an olefin, which process comprises reacting a feed comprising an olefin and oxygen in the presence of a catalyst which has been obtained by a process which comprises depositing silver on a carrier, wherein the carrier has been obtained by a method which comprises forming a mixture comprising:
a) from 50 to 95 weight percent of a first particulate α-alumina having a $d_{50}$ of from 5 to 100 μm;
b) from 5 to 50 weight percent of a second particulate α-alumina having a $d_{50}$ which is less than the $d_{50}$ of the first particulate α-alumina and which is in the range of from 1 to 10 μm; and c) an alkaline earth metal silicate bond material;
weight percent being based on the total weight of α-alumina in the mixture; and firing the mixture to form the carrier.

The invention also provides a process for preparing a 1,2-diol, a 1,2-diol ether or an alkanolamine comprising converting the olefin oxide into the 1,2-diol, the 1,2-diol ether or the alkanolamine wherein the olefin oxide has been obtained by a process for the epoxidation of an olefin in accordance with this invention.

DETAILED DESCRIPTION OF THE INVENTION

In accordance with the teaching of this invention, by maximizing for certain high-surface area carriers the number of pores having a diameter in the range of 0.3 to 10 μm, in particular by minimizing the pore volume in pores having diameters less than 0.3 μm, the catalyst based on the carrier is advantaged over catalysts that are prepared from carriers which have a substantial pore volume in pores having diameters less than 0.3 μm. In particular, catalysts prepared according to this invention show excellent activity and selectivity, and they are believed to provide significant improvements in stability under conditions of commercial operation. This is non-obvious in view of the prior art acknowledged hereinbefore. US 2003/0162984 A1 teaches improved performance of catalysts based on carriers having at least 1 $m^2/g$ surface area and having at least 70% of the total pore volume contained in pore with diameters in the range of from 0.2 to 10 μm. The teaching of US 2003/0162984 is such that a skilled person would utilize carriers with, in particular, a minimized number of pores having diameters greater than 10 μm. The reference does not contain teaching relevant to the pore size distribution within the range of pore diameters from 0.2 to 10 μm, and it does not contain teaching relevant to the stability of the catalysts, for example, under conditions of commercial operation.

"Surface area" as used herein is understood to refer to the surface area as determined by the nitrogen BET (Brunauer, Emmett and Teller) method as described in Journal of the American Chemical Society 60 (1938) pp. 309-316.

As used herein, water absorption is deemed to have been measured in accordance with ASTM C393, and water absorption is expressed as the weight of the water that can be absorbed into the pores of the carrier, relative to the weight of the carrier.

The pore size distribution may be measured by a conventional mercury intrusion porosimetry device in which liquid mercury is forced into the pores of a carrier. Greater pressure is needed to force the mercury into the smaller pores and the measurement of pressure increments corresponds to volume increments in the pores penetrated and hence to the size of the pores in the incremental volume. As used herein, the pore size distribution, the median pore diameters and the pore volumes are as measured by mercury intrusion porosimetry to a pressure of $2.1 \times 10^8$ Pa using a Micromeretics Autopore 9200 model (130° contact angle, mercury with a surface tension of 0.480 N/m, and correction for mercury compression applied). As used herein, the median pore diameter is the pore diameter at which half of the total pore volume is contained in pores having a larger pore diameter and half of the total pore volume is contained in pores having a smaller pore diameter.

The median particle size, referred to herein as "$d_{50}$", is as measured by a Horiba LA900 particle size analyzer and represents a particle diameter at which there are equal spherical equivalent volumes of particles larger and particles smaller than the stated median particle size. The method includes dispersing the particles by ultrasonic treatment, thus breaking up secondary particles into primary particles. This sonification treatment is continued until no further change in the $d_{50}$ value is noticed, which typically requires a 5 minute sonification when using the Horiba LA900 particle size analyzer.

As used herein, pore volume (ml/g), surface area ($m^2/g$) and water absorption (g/g) are defined relative to the weight of the carrier, unless stated otherwise.

In accordance with this invention, a carrier is used which has a pore size distribution such that at least 80% of the total pore volume is contained in pores with diameters in the range of from 0.1 to 10 μm, and at least 80% of the pore volume contained in the pores with diameters in the range of from 0.1 to 10 μm is contained in pores with diameters in the range of from 0.3 to 10 μm. Preferably, the pore size distribution is such that the pores with diameters in the range of from 0.1 to 10 μm represent at least 85%, in particular at least 90%, more preferably at least 95% of the total pore volume. Typically, the pore size distribution is such that pores with diameters less than 0.1 μm represent less than 10%, more typically at most 7%, in particular at most 5%, more in particular at most 1%, or even at most 0.5% or at most 0.1% of the total pore volume. Typically, the pore size distribution is such that pores with diameters greater than 10 μm represent less than 10%, in particular at most 8%, more in particular at most 6%, of the total pore volume.

Frequently, the pore size distribution is such that the pores with diameters in the range of from 0.1 to 10 μm represent less than 99.9%, more frequently less than 99%, most frequently less than 98% of the total pore volume. Frequently, the pores with diameters greater than 10 μm represent more than 0.1%, more frequently more than 0.5% of the total pore volume. The invention contemplates pores with diameters less than 0.1 μm approaching, if not reaching, zero percent of the total pore volume.

Typically, the pore size distribution is such that the pores with diameters in the range of 0.3 to 10 μm represent at least 85%, in particular at least 90%, more in particular at least 95% of the pore volume contained in the pores with diameters in the range of from 0.1 to 10 μm.

Typically, the pore size distribution is such that pores with diameters less than 0.3 μm represent less than 15%, more typically at most 10%, in particular at most 5%, more in particular at most 3% of the total pore volume. Frequently, the pore size distribution is such that pores with diameters less than 0.3 μm represent more than 0.01%, more frequently more than 0.1% of the total pore volume.

In another embodiment, the pore size distribution is such that the pores with diameters in the range of from 0.4 to 10 μm represent at least 75%, in particular at least 80% of the pore volume contained in the pores with diameters in the range of from 0.1 to 10 μm. In another embodiment, the pore size distribution is such that the pores with diameters in the range of from 0.5 to 10 μm represent at least 60%, in particular at least 65% of the pore volume contained in the pores with diameters in the range of from 0.1 to 10 μm.

In another embodiment, the pore size distribution is such that the pores with diameters in the range of from 2 to 10 μm represent at least 20%, more typically at least 30%, in particular at least 40% of the pore volume contained in the pores with diameters ranging from 0.1 to 10 μm. In another embodiment, the pore size distribution is such that the pores with diameters in the range of from 5 to 10 μm represent at least 15%, more typically at least 20% of the pore volume contained in the pores with diameters ranging from 0.1 to 10 μm.

The carriers may have a median pore diameter of more than 0.8 μm, preferably at least 0.85 μm, more preferably at least 0.9 μm. Typically, the median pore diameter is at most 2.1 μm, more typically at most 2 μm, in particular at most 1.9 μm. Preferably, the median pore diameter is in the range of from 0.85 to 1.9 μm, more preferably in the range of from 0.9 to 1.8 μm.

The total pore volume of the carrier may vary between wide ranges. Typically the total pore volume is at least 0.25 ml/g, in particular at least 0.3 ml/g, more in particular at least 0.35 ml/g. Typically, the total pore volume is at most 0.8 ml/g, and more typically it is at most 0.7 ml/g, in particular at most 0.6 ml/g.

The surface area of the carrier may be at least 1.3 $m^2/g$. Typically, the surface area is at most 5 $m^2/g$. Preferably, the surface area is in the range of from 1.3 to 3 $m^2/g$, more preferably from 1.4 to 2.5 $m^2/g$, most preferably from 1.5 to 2.2 $m^2/g$, for example from 1.5 to 2 $m^2/g$.

The water absorption of the carrier is typically at least 0.3 g/g, more typically at least 0.35 g/g. Frequently, the water absorption is at most 0.8 g/g, more frequently at most 0.7 g/g, or at most 0.6 g/g, or at most 0.55 g/g. Preferably, the water absorption of the carrier is in the range of from 0.3 to 0.7 g/g, in particular from 0.35 to 0.55 g/g. A higher water absorption and a higher total pore volume are in favor in view of a more efficient deposition of silver and further elements, if any, on the carrier by impregnation. However, at a higher water absorption and higher total pore volume, the carrier, or the catalyst made therefrom, may have lower crush strength.

In certain embodiments of this invention, the carrier exhibits a non-platelet morphology. As used herein, the term "non-platelet morphology" refers to the morphology of the carrier when imaged by scanning electron microscopy at a magnification of 2000, and to the substantial absence in such images of structures having substantially flat surfaces. By "substantial absence" of such structures it is meant that at most 25% of the structures have a substantially flat surface. By "substantially flat" it is meant that the radius of the curvature of the surface is at least 2 times the length of the largest dimension of the surface. The structures having a substantially flat surface have typically an aspect ratio of at most 4:1, the aspect ratio of a structure being the ratio of the largest dimension to the smallest dimension of the structure. The term "structures" refers to structural entities in the carrier which can be designated to represent individual particles of carrier material fused or bonded together to form the carrier.

The carrier may be based on a wide range of materials. Such materials may be natural or artificial inorganic materials and they may include refractory materials, silicon carbide, clays, zeolites, charcoal and alkaline earth metal carbonates, for example calcium carbonate. Preferred are refractory materials, such as alumina, magnesia, zirconia and silica. The most preferred material is α-alumina. Typically, the carrier comprises at least 85 weight percent, more typically 90 weight percent, in particular 95 weight percent α-alumina, frequently up to 99.9 weight percent α-alumina.

Carriers may generally be made by firing particulate components at an elevated temperature until the particles sinter together. In general; firing may be continued until the particles are bonded together, either by the formation of bond posts from any added bond material or through sintering, but preferably not beyond the point at which the water absorption of the carrier is reduced.

Burnout materials may or may not be used in the firing process. Burnout materials are well known in the art (cf., for example, F F Y Wang (Ed.), "Treatise on Materials Science and Technology", Volume 9, (New York, 1976), pp. 79-81; or J S Reed, "Introduction to the Principles of Ceramic Processing", (New York, 1988), pp. 152 ff.). The burnout materials may be used to enhance preservation of the structure during a green, i.e. unfired, phase of the carrier preparation, for example the phase in which formed bodies are shaped, for example by extrusion. The burnout materials are removed during the firing. The use of burnout materials also allows more complete sintering without too great a reduction in water absorption of the carrier. The burnout materials are typically finely divided solid organic materials that volatilize or burn, leaving as little residue as possible.

It is also a common expedient to use a bond material, i.e. a material which reduces the length of sintering time applied to bond the particles together. The bond material may also form a coating on at least a part of the carrier surface, which makes the carrier surface more receptive. The bond material may be based on a silica-containing composition comprising a crystallization inhibitor, inhibiting the formation of crystalline silica-containing compositions.

The silica-containing compositions for use as a bond material may comprise an alkali metal silicate bond material, or preferably an alkaline earth metal silicate bond material. The bond material may further comprise a hydrated alumina and optionally a titanium component and/or a zirconium component.

It has been found that, suitably, alumina carriers for use in this invention may be made by a method which comprises forming a mixture comprising:

a) from 50 to 95 weight percent of a first particulate α-alumina having a $d_{50}$ of from 5 to 100 μm, in particular from 8 to 60 μm, more in particular from 10 to 40 μm;

b) from 5 to 50 weight percent of a second particulate α-alumina having a $d_{50}$ which is less than the $d_{50}$ of the first particulate α-alumina and which is in the range of from 1 to 10 μm, in particular from 2 to 8 μm; and preferably in addition c) an alkaline earth metal silicate bond material;

weight percent being based on the total weight of α-alumina in the mixture; and then shaping the mixture into formed bodies and firing the formed bodies, typically at a temperature of from 1250 to 1550° C., to form the carrier.

The present method for making alumina carriers is well adapted to produce the carriers for use in this invention, in view of the careful matching of large and small particles of the α-alumina components. The alumina particles are readily commercially available, or they may readily be made, for example, by subjecting more coarse materials to grinding and sieving operations. In an embodiment, the smaller particles may be prepared from the larger particles by grinding, and the ground and un-ground particles are then combined. In another embodiment, the desired mixture of large and small particles may be formed by grinding relatively large particles to the extent that the mixture of particles has the desired bimodal particle size distribution.

Typically, the first particulate α-alumina is employed in a quantity of from 60 to 90 weight percent, relative to the total weight of α-alumina in the mixture. Typically, the second particulate α-alumina is employed in a quantity of from 10 to 40 weight percent, relative to the total weight of α-alumina in the mixture.

In one embodiment, a carrier of this invention can be made using alumina powders, designated above as the "first particulate" and the "second particulate", that are characterized as follows. The first particulate powder has a BET surface area of 4.3 $m^2/g$, a $d_{50}$ median particle size of 15 μm and a pore size distribution wherein pores having diameters less than 0.3 μm, and preferably less than 0.2 μm, contribute less than 4 percent of the first particulate powder's total pore volume.

The second particulate powder has a surface area of 1.4 m²/g, a $d_{50}$ median particle size of 3.1 µm and a pore size distribution wherein pores having diameters less than 0.3 µm, and preferably less than 0.2 µm, contribute less than 1 percent of the second particulate powder's total pore volume. The first and second powders' pore size distributions and pore volumes can be measured by mercury intrusion porosimetry beginning at 2413 Pa and then increased to $4.1 \times 10^7$ Pa using a Micromeretics Model 9520 Autopore IV (130° contact angle, mercury with a surface tension of 0.48 m²/g, and correction for mercury compression applied). The alumina powders selected for use in making a carrier can impact the physical characteristics, such as pore size distribution and total pore volume, of the carrier. Reducing the percentage of the first and second alumina powders' pore volumes contributed by pores less than 0.3 µm is believed to result in a carrier with a minimum quantity of its total pore volume contributed by small pores.

The alkaline earth metal silicate bond material may comprise an alkaline earth metal silicate, for example calcium silicate or, preferably, magnesium silicate. Alternatively to or in addition to the alkaline earth metal silicate, the alkaline earth metal silicate bond material may comprise a combination of an alkaline earth metal compound and a silica compound. In such combination the atomic ratio of the alkaline earth metal to silicon is typically in the range of from 0.5 to 2, more typically 0.8 to 1.4 and most typically 0.9 to 1.2. Suitable alkaline earth metal compounds are alkaline earth metal salts, for example nitrates or sulfates, in particular magnesium nitrate or magnesium sulfate. Suitable silica compounds are silica sol, precipitated silica, amorphous silica, amorphous alkali metal silica, or amorphous alkali metal aluminosilicate. Amorphous silica compounds are preferred. The quantity of alkaline earth metal silicate bond material may suitably be in the range of from 0.2 to 10 weight percent, more suitably from 0.2 to 2 weight percent, in particular from 0.5 to 2 weight percent, calculated as the total weight of alkaline earth metal oxide and silicate, as $SiO_2$, relative to the total weight of α-alumina in the mixture.

The alkaline earth metal silicate bond material may or may not comprise, as an additional component, a hydrated alumina. A suitable hydrated alumina is, for example, gibbsite, bayerite or diaspore. A preferred hydrated alumina is boehmite. The quantity of the hydrated alumina may suitably be in the range of from 0.1 to 15 weight percent, from 0.2 to 10 weight percent, or from 0.5 to 5 weight percent, calculated as the weight of aluminium oxide, $Al_2O_3$, relative to the total weight of α-alumina in the mixture.

The alkaline earth metal silicate bond material may or may not comprise, as an additional component, a zirconium component, as a solid component or as a liquid component. Suitable zirconium components are zirconium dioxide and zirconium compounds which convert to zirconium dioxide upon firing. Such zirconium compounds may be salts, such as zirconyl nitrate, zirconyl sulfate or basic zirconyl carbonate. The quantity of the zirconium component may suitably be in the range of from 0 to 10 weight percent, more suitably from 0.2 to 5 weight percent, calculated as the weight of zirconium dioxide, $ZrO_2$, relative to the total weight of α-alumina in the mixture.

The alkaline earth metal silicate bond material may or may not comprise, as an additional component, a titanium component. Suitable titanium components are titanium dioxide, titanyl sulfate, titanyl oxalate, titanyl chloride, organo titanates, and other compounds which convert to titanium dioxide upon firing. Hydrated aluminas may in some instances be contaminated with titanium compounds and act as a source of the titanium component. The quantity of the titanium component may suitably be in the range of from 0 to 5 weight percent, more suitably from 0 to 1 weight percent, even more suitably from 0.01 to 0.5 weight percent, in particular from 0.1 to 0.3 weight percent, calculated as the weight of titanium dioxide, $TiO_2$, relative to the total weight of α-alumina in the mixture.

In an embodiment, the alkali metal silicate bond material may comprise an alkali metal silicate, for example amorphous sodium or lithium silicate.

Burnout materials may be selected from the group of polypropylenes, polyethylenes, carbohydrates, gums, flours, proteins, lignins, resins, waxes, alcohols, and esters. When preparing an α-alumina carrier, the quantity of burnout material may suitably be in the range of from 0.2 to 10 weight percent, more suitably from 0.5 to 5 weight percent, relative to the total weight of α-alumina in the mixture. The selection of the burnout material is considered not to be of any criticality to the invention. Also, in the practice of this invention using an α-alumina carrier, no burnout material may be used in the preparation of the carrier.

It is also preferred that the carrier particles be prepared in the form of formed bodies, the size of which is in general determined by the dimensions of an epoxidation reactor in which they are to be deposited. Generally however it is found very convenient to use particles such as formed bodies in the form of powder, trapezoidal bodies, cylinders, saddles, spheres, doughnuts, and the like. The cylinders may be solid or hollow, straight or bent, and they may have their length and cross-sectional dimensions about the same and from 5 to 10 mm.

The formed bodies can be formed from the mixture by any convenient forming process, such as spraying, spray drying, agglomeration or pressing, but preferably they are formed by extrusion of the mixture. For applicable methods, reference may be made to, for example, U.S. Pat. No. 5,145,824, U.S. Pat. No. 5,512,530, U.S. Pat. No. 5,384,302, U.S. Pat. No. 5,100,859 and U.S. Pat. No. 5,733,842, which are herein incorporated by reference. To facilitate such molding processes, in particular extrusion, the mixture may suitably be compounded with up to about 30 weight percent and preferably from 2 to 25 weight percent, based on the weight of the mixture, of extrusion aids and/or organic binders. Extrusion aids (also referred to by the term "processing aids") and organic binders are known in the art (cf., for example, "Kirk-Othmer Encyclopedia of Chemical Technology", 4th edition, Volume 5, pp. 610 ff.). Suitable examples may be petroleum jelly, hydrogenated oil, synthetic alcohol, synthetic ester, glycol, starch, polyolefin oxide or polyethylene glycol. Boric acid may also be added to the mixture, for example in a quantity of up to 0.5 weight percent, more typically in a quantity of from 0.01 to 0.5 weight percent, based on the weight of the mixture. The effect of the presence of boric acid may be a reduced content of leachable alkali metal ions in the carrier after firing. Enough water may be added to the mixture to make the mixture extrudable (by the term "the weight of the mixture", as used hereinbefore, is meant the weight of the total mixture, but excluding the weight of any added water).

The formed bodies may be dried and fired at a temperature high enough to ensure that the alumina particles are joined together by a sintering action and/or by the formation of bond posts formed from the bond material, if incorporated in the mixture. Generally, drying may take place between 20 and 400° C. and preferably between 30 and 300° C., typically for a period of up to 100 hours and preferably from 5 minutes to 50 hours. Typically, drying is performed to the extent that the mixture contains less than 2 weight percent of water. Generally, firing may take place at a temperature of at least 1250° C., preferably between 1250 and 1550° C., typically between 1300 and 1530° C., in particular between 1300 and 1520° C., typically for a period of up to about 8 hours and preferably from 2 to 6 hours. Drying and firing may be carried out in any atmosphere, such as in air, nitrogen, or helium, or mixtures thereof. Preferably, in particular when the formed bodies contain organic material, the firing is at least in part or entirely carried out in an oxidizing atmosphere, such as in an oxygen-containing atmosphere.

The performance of the catalyst may be enhanced if the carrier is washed, to remove soluble residues, before deposition of other catalyst ingredients on the carrier. On the other hand, unwashed carriers may also be used successfully. A useful method for washing the carrier comprises washing the carrier in a continuous fashion with hot, demineralised water, until the electrical conductivity of the effluent water does not further decrease. A suitable temperature of the demineralised water is in the range of 80 to 100° C., for example 90° C. or 95° C. Reference may be made to WO-00/15333 and U.S. Pat. No. 6,368,998, which are incorporated herein by reference.

Generally, the catalyst of this invention comprises silver as a catalytically active metal. Appreciable catalytic activity is obtained by employing a silver content of the catalyst of at least 10 g/kg, in particular at least 50 g/kg, relative to the weight of the catalyst. The preparation of the catalysts is known in the art and the known methods are applicable to the preparation of the catalyst of this invention. Methods of preparing the catalyst include impregnating the carrier with a silver compound and performing a reduction to form metallic silver particles. Catalysts having relatively high silver content may be prepared by multiple impregnation, for example double or triple impregnation. Reference may be made, for example, to U.S. Pat. No. 5,380,697, U.S. Pat. No. 5,739,075, U.S. Pat. No. 6,368,998, US-2002/0010094 A1, EP-A-266015, WO-00/15333, WO-00/15334 and WO-00/15335, which are incorporated herein by reference.

The impregnation may include impregnation with a solution of which the pH has a value above 12, for example 13 or 13.2 or above. This may be accomplished by the addition of a base to the impregnation solution, for example lithium hydroxide, cesium hydroxide or a tetraalkylammonium hydroxide, such as tetramethylammonium hydroxide or tetraethylammonium hydroxide, in sufficient quantity. Dependent of the composition of the impregnation solution, a quantity of base in the range of from 20 to 70 mmole/kg carrier, for example 30, 40, 50 or 60 mmole/kg carrier may be sufficient to achieve a sufficiently high pH.

The reduction of cationic silver to metallic silver may be accomplished during a step in which the catalyst is dried, so that the reduction as such does require a separate process step. This may be the case if the impregnation solution comprises a reducing agent, for example, an oxalate, as described in the Examples hereinafter.

The catalyst preferably comprises silver, and a further element or compound thereof. Eligible further elements may be selected from the group of nitrogen, sulfur, phosphorus, boron, fluorine, Group IA metals, Group IIA metals, rhenium, molybdenum, tungsten, chromium, titanium, hafnium, zirconium, vanadium, manganese, thallium, thorium, tantalum, niobium, gallium and germanium and mixtures thereof. Preferably the Group IA metals are selected from lithium, potassium, rubidium and cesium. Most preferably the Group IA metal is lithium, potassium and/or cesium. Preferably the Group IIA metals are selected from calcium and barium. Where possible, the further element may suitably be provided as an oxyanion, for example, as a sulfate, borate, perrhenate, molybdate or nitrate, in salt or acid form.

It is preferred to employ the carrier of this invention in the preparation of a highly selective catalyst. The highly selective silver-based catalysts may comprise, in addition to silver, one or more of rhenium, molybdenum, tungsten, a Group IA metal, and a nitrate- or nitrite-forming compound, which may each be present in a quantity of from 0.01 to 500 mmole/kg, calculated as the element (rhenium, molybdenum, tungsten, the Group IA metal or nitrogen) on the total catalyst. The nitrate- or nitrite-forming compounds and particular selections of nitrate- or nitrite-forming compounds are as defined hereinafter. The nitrate- or nitrite-forming compound is in particular a Group IA metal nitrate or a Group IA metal nitrite. Rhenium, molybdenum, tungsten or the nitrate- or nitrite-forming compound may suitably be provided as an oxyanion, for example as a perrhenate, molybdate, tungstate or nitrate, in salt or acid form.

Of special preference are the highly selective catalysts which comprise rhenium in addition to silver. Such catalysts are known from EP-A-266015, U.S. Pat. No. 4,761,394 and U.S. Pat. No. 4,766,105, which are incorporated herein by reference. Broadly, they comprise silver, rhenium or compound thereof, the further element (as defined hereinbefore, in particular tungsten, molybdenum and/or a Group IA metal, in particular lithium and/or cesium) other than rhenium or compound thereof, and optionally a rhenium co-promoter. The rhenium co-promoter may be selected from one or more of sulfur, phosphorus, boron, and compounds thereof.

Preferred amounts of the components of the catalysts are, when calculated as the element, relative to the weight of the catalyst:

silver from 10 to 500 g/kg,
rhenium from 0.01 to 50 mmole/kg, if present,
the further element or elements, if present, each from 0.1 to 500 mmole/kg, and,
the rhenium co-promoter from 0.1 to 30 mmole/kg, if present.

With respect to silver, this metal is present preferably in an amount of 50 to 500 g/kg, more preferably 50 to 400 g/kg, in particular 50 to 350 g/kg, for example 105 g/kg, or 120 g/kg, or 145 g/kg, or 191 g/kg, or 200 g/kg, or 250 g/kg, or 290 g/kg, or 310 g/kg. Rhenium may preferably be present in an amount of from 0.1 to 10 mmoles/kg, for example 2 mmoles/kg, or 3 mmoles/kg, or 5 mmoles/kg. The further element or elements may each be present in a preferred amount of from 0.5 to 100 mmole/kg. For example, tungsten may typically be present in an amount in the range of from 0.5 to 20 mmole/kg, such as 1 mmole/kg, or 1.5 mmoles/kg, or 5 mmole/kg, or 15 mmole/kg; molybdenum may typically be present in an amount in the range of from 1 to 40 mmole/kg, such as 2.3 mmole/kg, or 12 mmole/kg, or 25 mmole/kg; and the alkali metal may each typically be present in amount of from 5 to 100 mmole/kg. Suitable amounts for lithium are for example 5 mmole/kg, or 10 mmole/kg, or 22.2 mmole/kg, or 30 mmole/kg, or 40 mmole/kg, or 50 mmole/kg. Suitable amounts for cesium are for example 5 mmole/kg, or 5.3 mmole/kg, or 5.4 mmole/kg, or 6.1 mmole/kg, or 6.2 mmole/kg, or 6.4 mmole/kg, or 7.2 mmole/kg, or 7.5 mmole/kg, or 10 mmole/kg, or 15 mmole/kg, or 33 mmole/kg, or 47 mmole/kg.

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Mixtures of olefins may be used. Typically, the olefin is a monoolefin, for example 2-butene or isobutene. Preferably, the olefin is a mono-α-olefin, for example 1-butene or propylene. The most preferred olefin is ethylene.

The olefin concentration in the feed may be selected within a wide range. Typically, the olefin concentration in the feed will be at most 80 mole percent, relative to the total feed. Preferably, it will be in the range of from 0.5 to 70 mole percent, in particular from 1 to 60 mole percent, on the same basis. As used herein, the feed is considered to be the composition which is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process air or air enriched with oxygen is employed as the source of the oxidizing agent while in the oxygen-based processes high-purity (at least 95 mole percent) oxygen is employed as the source of the oxidizing agent. Presently most epoxidation plants are oxygen-based and this is a preferred embodiment of the present invention.

The oxygen concentration in the feed may be selected within a wide range. However, in practice, oxygen is generally applied at a concentration which avoids the flammable regime. Typically, the concentration of oxygen applied will be within the range of from 1 to 15 mole percent, more typically from 2 to 12 mole percent of the total feed.

In order to remain outside the flammable regime, the concentration of oxygen in the feed may be lowered as the concentration of the olefin is increased. The actual safe operating ranges depend, along with the feed composition, also on the reaction conditions such as the reaction temperature and the pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifier. Nitrogen oxides, hydrazine, hydroxylamine or ammonia may be employed as well. It is frequently considered that under the operating conditions of olefin epoxidation the nitrogen containing reaction modifiers are precursors of nitrates or nitrites, i.e. they are so-called nitrate- or nitrite-forming compounds (cf. e.g. EP-A-3642 and U.S. Pat. No. 4,822,900, which are incorporated herein by reference).

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in low concentration in the feed, for example up to 0.1 mole percent, relative to the total feed, for example from $0.01 \times 10^{-4}$ to 0.01 mole percent. In particular when the olefin is ethylene, it is preferred that the reaction modifier is present in the feed at a concentration of from $0.1 \times 10^{-4}$ to $50 \times 10^{-4}$ mole percent, in particular from $0.3 \times 10^{-4}$ to $30 \times 10^{-4}$ mole percent, relative to the total feed.

In addition to the olefin, oxygen and the reaction modifier, the feed may contain one or more optional components, such as carbon dioxide, inert gases and saturated hydrocarbons. Carbon dioxide is a by-product in the epoxidation process. However, carbon dioxide generally has an adverse effect on the catalyst activity. Typically, a concentration of carbon dioxide in the feed in excess of 25 mole percent, preferably in excess of 10 mole percent, relative to the total feed, is avoided. A concentration of carbon dioxide as low as 1 mole percent or lower, relative to the total feed, may be employed. A suitable concentration of carbon monoxide may be in the range of from 0.2 to 0.8 mole percent, for example 0.5 mole percent, relative to the total feed. Inert gases, for example nitrogen or argon, may be present in the feed in a concentration of from 30 to 90 mole percent, typically from 40 to 80 mole percent. Suitable saturated hydrocarbons are methane and ethane. If saturated hydrocarbons are present, they may be present in a quantity of up to 80 mole percent, relative to the total feed, in particular up to 75 mole percent. Frequently they are present in a quantity of at least 30 mole percent, more frequently at least 40 mole percent. Saturated hydrocarbons may be added to the feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is as a gas phase process involving a packed catalyst bed, the GHSV is in the range of from 1500 to 10000 Nl/(l·h). Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour, for example 5 kmole olefin oxide produced per $m^3$ of catalyst per hour. As used herein, the work rate is the amount of the olefin oxide produced per unit volume of catalyst per hour and the selectivity is the molar quantity of the olefin oxide formed relative to the molar quantity of the olefin converted.

The olefin oxide produced may be recovered from the reaction mixture by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol or a 1,2-diol ether.

The olefin oxide produced in the epoxidation process may be converted into a 1,2-diol, a 1,2-diol ether, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1 weight percent sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise, for example, reacting the olefin oxide with ammonia. Anhydrous or aqueous ammonia may be used, although anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the low-molecular weight organic compounds mentioned herein, for example the olefins, 1,2-diols, 1,2-diol ethers, alkanolamines and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLES

Example 1

Preparation of Carriers

A carrier (designated hereinafter as "Carrier A") was made by mixing the following ingredients:

1. 75.8 parts by weight (pbw) of an α-alumina with $d_{50}$ of 21 μm;
2. 20 pbw of an α-alumina with $d_{50}$ of 3 μm;
3. 3 pbw of boehmite, calculated as $Al_2O_3$;
4. 0.2 pbw of magnesium silicate, calculated as $MgSiO_3$; and
5. 1 pbw of zirconium oxide.

To this mixture were added 10 weight percent, relative to the mixture weight, of petroleum jelly and 8 weight percent, relative to the mixture weight, of starch and 0.1 weight percent, relative to the mixture weight, of boric acid. Water was then added in an amount to make the mixture extrudable and this mixture was then extruded to form formed bodies in the form of hollow cylinders that are about 6 mm in diameter and 6 mm long. These were then dried and fired in a kiln at 1480° C., for 5 hours in air to produce Carrier A. As regards procedures followed in this carrier preparation, reference may be made to US 2003/0162984-A1.

A second carrier (hereinafter "Carrier B") was made by the same procedure as Carrier A, except that 75.8 parts by weight (pbw) of an α-alumina with $d_{50}$ of 15 μm was used instead of the α-alumina with $d_{50}$ of 21 μm.

A third carrier (hereinafter "Carrier C") was made by the same procedure as Carrier A, except that:

no zirconium dioxide was used;

76.8 parts by weight (pbw) of an α-alumina with $d_{50}$ of 15 μm was used instead of the α-alumina with $d_{50}$ of 21 μM; and firing was carried out at 1510° C., for 5 hours, instead of at 1480° C.

For comparative purposes, a fourth carrier (hereinafter "Carrier D") was prepared according to the process as described for "Carrier A" in the Examples of US 2003/0162984.

For comparative purposes, a fifth carrier (hereinafter "Carrier E") was made by the same procedure as Carrier A, except that:

no boehmite was used;

68.8 parts by weight (pbw) of an α-alumina with $d_{50}$ of 31 μm was used instead of the α-alumina with $d_{50}$ of 21 μm;

30 parts by weight (pbw) of an α-alumina with $d_{50}$ of 3 μm was used instead of 20 pbw; and firing was carried out at 1450° C., for 5 hours, instead of at 1480° C.

The carriers exhibited characteristics as indicated in Table I. The pore size distribution is specified as the volume fraction (volume percent) of the pores having diameters in the specified ranges (<0.1 μm, 0.1-10 μm, 0.1-0.3 μm, 0.2-0.3 μm, 0.3-10 μm, 5-10 μm, and >10 μm), relative to the total pore volume. "Pore volume" represents the total pore volume. "$D_{50}$" represents the median pore diameter.

TABLE I

| Carrier | Surface area (m²/g) | Water absorption (g/g) | Pore volume (ml/g) | $D_{50}$ (μm) | Pore size distribution (volume percent) *) | | | | | | |
|---|---|---|---|---|---|---|---|---|---|---|---|
| | | | | | <0.1 μm | 0.1-10 μm | 0.1-0.3 μm | 0.2-0.3 μm | 0.3-10 μm | >10 μm | 5-10 μm |
| A | 1.68 | 0.50 | 0.50 | 1.8 | <1 | 94 | 2 | 2 | 92 | 6 | 23 |
| B | 1.72 | 0.50 | 0.50 | 1.0 | <1 | 97 | 2 | 1 | 95 | 3 | 8 |
| C | 1.55 | 0.43 | 0.42 | 1.0 | <1 | 97 | 2 | 2 | 95 | 3 | 5 |
| D **) | 2.00 | 0.42 | 0.41 | 2.2 | <1 | 97 | 22 | 17 | 75 | 3 | 13 |
| E **) | 1.95 | 0.45 | 0.43 | 2.8 | <1 | 93 | 23 | 18 | 70 | 6 | 25 |

*) volume percent relative to the total pore volume
**) comparative

Example 2

Preparation of Catalysts

A silver-amine-oxalate stock solution was prepared by the following procedure:

415 g of reagent-grade sodium hydroxide were dissolved in 2340 ml de-ionized water and the temperature was adjusted to 50° C.

1699 g high purity "Spectropure" silver nitrate was dissolved in 2100 ml de-ionized water and the temperature was adjusted to 50° C.

The sodium hydroxide solution was added slowly to the silver nitrate solution, with stirring, while maintaining a solution temperature of 50° C. This mixture was stirred for 15 minutes, then the temperature was lowered to 40° C.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 µmho/cm. 1500 ml fresh deionized water was then added.

630 g of high-purity oxalic acid dihydrate were added in approximately 100 g increments. The temperature was kept at 40° C. and the pH was kept above 7.8.

Water was removed from this mixture to leave a highly concentrated silver-containing slurry. The silver oxalate slurry was cooled to 30° C.

699 g of 92 weight percent ethylenediamine (8% de-ionized water) was added while maintaining a temperature no greater than 30° C. The final solution was used as a stock silver impregnation solution for preparing the catalysts.

Carriers A, B, C, D, and E, prepared according to Example 1, were used to make silver catalysts, as follows, to form Catalyst A (according to the invention), Catalyst B (according to the invention) Catalyst C (according to the invention), Catalyst D (for comparison), and Catalyst E (for comparison), respectively. Actual silver and cesium loadings have been specified in Table II, hereinafter. Catalysts A, B, C, D, and E also contained 2.8 mmoles rhenium/kg catalyst, 12 mmoles lithium/kg catalyst, and 0.6 mmoles tungsten/kg catalyst.

Catalyst A (According to the Invention):

Catalyst A was prepared in two impregnation steps.

To 191 grams of stock impregnation solution of specific gravity 1.548 g/ml was added 13.0 grams of water, resulting in a solution with a specific gravity of 1.496 g/ml. A vessel containing 120 grams of Carrier A was evacuated to 20 mm Hg for 1 minute and the impregnation solution was added to Carrier A while under vacuum, then the vacuum was released and the carrier allowed to contact the liquid for 3 minutes. The impregnated Carrier A was then centrifuged at 500 rpm for 2 minutes to remove excess liquid. Impregnated Carrier A pellets were placed in a vibrating shaker and dried in air flowing at a rate of 16.2 Nl/h at 250° C. for 5.5 minutes. The resulting dried catalyst precursor contained approximately 17.2 weight percent silver.

The dried Catalyst A Precursor was then impregnated with a second solution which was made by mixing 191.0 grams of silver stock solution of specific gravity 1.548 g/ml with a solution of 0.2980 g of ammonium perrhenate in 2 g of 1:1 (w/w) ethylenediamine/water, 0.0594 g of ammonium metatungstate dissolved in 2 g of 1:1 ammonia/water and 0.3283 g lithium nitrate dissolved in water. Additional water was added to adjust the specific gravity of the solution to 1.496 g/ml. 50 grams of such doped solution was mixed with 0.1830 g of 46.07 weight percent cesium hydroxide solution. This final impregnation solution was used to prepare Catalyst A. A vessel containing 30 grams of the Catalyst A Precursor was evacuated to 20 mm Hg for 1 minute and the final impregnation solution was added while under vacuum, then the vacuum was released and the precursor allowed to contact the liquid for 3 minutes. The impregnated precursor was then centrifuged at 500 rpm for 2 minutes to remove excess liquid. Catalyst A pellets were placed in a vibrating shaker and dried in air flowing at a rate of 16.2 Nl/h at 250° C. for 5.5 minutes.

Catalyst B (According to the Invention):

Catalyst B was prepared in the same manner as Catalyst A, using 120 grams carrier B. The specific gravity of the impregnation solution in the first impregnation was 1.563. The dried Catalyst B Precursor was then impregnated with a second solution which was made by mixing 194.0 grams of silver stock solution of specific gravity 1.563 g/ml with a solution of 0.3160 g of ammonium perrhenate in 2 g of 1:1 (w/w) ethylenediamine/water, 0.0629 g of ammonium metatungstate dissolved in 2 g of 1:1 ammonia/water and 0.3481 g lithium nitrate dissolved in water. Additional water was added to adjust the specific gravity of the solution to 1.521 g/ml. The total water added was 10.0 grams. 50 grams of such doped solution was mixed with 0.1827 g of 46.07 weight percent cesium hydroxide solution. This final impregnation solution was used to prepare Catalyst B.

Catalyst C (According to the Invention):

Catalyst C was prepared in the same manner as Catalyst A, using 120 grams carrier C. The specific gravity of the impregnation solution in the first impregnation was 1.552. The dried Catalyst C Precursor was then impregnated with a second solution which was made by mixing 232 grams of silver stock solution of specific gravity 1.552 g/ml with a solution of 0.4077 g of ammonium perrhenate in 2 g of 1:1 (w/w) ethylenediamine/water, 0.0812 g of ammonium metatungstate dissolved in 2 g of 1:1 ammonia/water and 0.4491 g lithium nitrate dissolved in water. Additional water was added to adjust the specific gravity of the solution to 1.511 g/ml. The total water added was 11.9 grams. 50 grams of such doped solution was mixed with 0.2534 g of 46.07 weight percent cesium hydroxide solution. This final impregnation solution was used to prepare Catalyst C.

Catalyst D (Comparative):

Catalyst D was prepared in the same manner as Catalyst A, using 120 grams carrier D. The specific gravity of the impregnation solution in the first impregnation was 1.529 g/ml. The dried Catalyst D Precursor was then impregnated with a second solution which was made by mixing 199.3 grams of silver stock solution of specific gravity 1.548 g/ml with a solution of 0.3370 g of ammonium perrhenate in 2 g of 1:1 (w/w) ethylenediamine/water, 0.0671 g of ammonium metatungstate dissolved in 2 g of 1:1 ammonia/water and 0.3713 g lithium nitrate dissolved in water. Additional water was added to adjust the specific gravity of the solution to 1.529 g/ml. The total water added was 4.7 grams. 50 grams of such doped solution was mixed with 0.2435 g of 46.07 weight percent cesium hydroxide solution. This final impregnation solution was used to prepare Catalyst D.

Catalyst E (Comparative):

Catalyst E was prepared in the same manner as Catalyst A, using 120 grams carrier E. The specific gravity of the impregnation solution in the first impregnation was 1.527 g/ml. The dried Catalyst E Precursor was then impregnated with a second solution which was made by mixing 199.0 grams of silver stock solution of specific gravity 1.548 g/ml with a solution of 0.3218 g of ammonium perrhenate in 2 g of 1:1 (w/w) ethylenediamine/water, 0.0641 g of ammonium metatungstate dissolved in 2 g of 1:1 ammonia/water and 0.3545 g lithium nitrate dissolved in water. Additional water was added to adjust the specific gravity of the solution to 1.527 g/ml. The total water added was 5.0 grams. 50 grams of such doped solution was mixed with 0.2093 g of 46.07 weight percent cesium hydroxide solution. This final impregnation solution was used to prepare Catalyst E.

TABLE II

| Catalyst | Cesium Content (mmoles/kg) | Silver Content % w |
|---|---|---|
| A *) | 6.4 | 29.0 |
| B *) | 6.2 | 30.7 |
| C *) | 6.5 | 27.0 |
| D **) | 7.5 | 26.8 |
| E **) | 6.8 | 28.0 |

*) invention
**) comparative

Example 3

Testing of Catalysts

The catalysts were used to produce ethylene oxide from ethylene and oxygen. To do this, crushed catalyst were loaded into a stainless steel U-shaped tube. The tube was immersed in a molten metal bath (heat medium) and the ends were connected to a gas flow system. The weight of catalyst used and the inlet gas flow rate (0.28 Nl/minute) were adjusted to give a gas hourly space velocity of 3300 Nl/(l·h), as calculated for uncrushed catalyst. The inlet gas pressure was 1550 kPa (absolute).

The gas mixture passed through the catalyst bed, in a "once-through" operation, during the entire test run including the start-up, consisted of 30.0 volume percent ethylene, 8.0 volume percent oxygen, 5.0 volume percent carbon dioxide, 57 volume percent nitrogen and 1.0 to 6.0 parts per million by volume (ppmv) ethyl chloride.

The initial reactor temperature was 180° C., and this was ramped up at a rate of 10° C. per hour to 225° C. and then adjusted so as to achieve a constant ethylene oxide content of 3.1 volume percent in the outlet gas stream at an ethyl chloride concentration of 1.3 ppmv. Performance data at this conversion level are usually obtained for initial peak selectivity. Depending upon the catalyst used and the parameters of the olefin epoxidation process, the time required to reach the initial, peak selectivity, that is the highest selectivity reached in the initial stage of the process, may vary. For example, the initial, peak selectivity of a process may be achieved after only 1 or 2 days of operation or may be achieved after as much as, for example, 1 month of operation. In the testing of Catalysts A, B, C, D, and E, the activity and selectivity were also measured upon continued operation. The results obtained after a cumulative production of ethylene oxide of 0.5 kton/m$^3$ and 1 kton/m$^3$ of catalyst are also reported in Table III.

An advantage of the present invention is that catalysts made according to this invention exhibit increased initial selectivity at the same ethylene oxide production levels. Also, the present invention exhibits improved stability.

TABLE III

| Catalyst | Selectivity (%) | Temperature (° C.) |
|---|---|---|
| A *), initially | 88.0 | 247 |
| at 0.5 kton/m$^3$ | 87.6 | 253 |
| at 1 kton/m$^3$ | 86.2 | 257 |
| B *), initially | 87.6 | 251 |
| at 0.5 kton/m$^3$ | 87.6 | 253 |
| at 1 kton/m$^3$ | 86.1 | 263 |
| C *), initially | 89.1 | 251 |
| at 0.5 kton/m$^3$ | 88.7 | 254 |
| at 1 kton/m$^3$ | 87.9 | 257 |
| D **), initially | 85.7 | 247 |
| at 0.5 kton/m$^3$ | 84.8 | 251 |
| at 1 kton/m$^3$ | 83.5 | 255 |
| E **), initially | 86.8 | 255 |
| at 0.5 kton/m$^3$ | 85.2 | 257 |
| at 1 kton/m$^3$ | 82.7 | 267 |

*) invention
**) comparative

What is claimed is:

1. A process for the epoxidation of an olefin, which process comprises reacting a feed comprising an olefin and oxygen in the presence of a catalyst comprising a carrier and silver deposited on the carrier, which carrier comprises at least 85 weight percent α-alumina and has a surface area of at least 1.3 m$^2$/g, a median pore diameter of more than 0.8 μm, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

2. A process as claimed in claim 1, wherein the olefin is ethylene.

3. A process as claimed in claim 1, wherein the feed further comprises a reaction modifier selected from the group consisting of organic halides, organic nitrogen compounds, nitrogen oxides, hydrazine, hydroxylamine and ammonia.

4. A process as claimed in claim 1, wherein the feed additionally comprises carbon dioxide in a concentration of above 1 mole percent, relative to the total feed.

5. A process as claimed in claim 1, wherein the feed additionally comprises carbon dioxide in a concentration of 1 mole percent or lower, relative to the total feed.

6. A process as claimed in claim 1, wherein an olefin oxide is formed at a work rate in the range of from 0.5 to 10 kmole olefin oxide per m$^3$ of catalyst per hour.

7. A process as claimed in claim 1 wherein the carrier has a pore size distribution such that at least 90% of the total pore volume is contained in the pores with diameters in the range of from 0.1 to 10 μm; at least 90% of the pore volume contained in the pores with diameters in the range of from 0.1 to 10 μm is contained in pores with diameters in the range of from 0.3 to 10 μm; the pores with diameters greater than 10 μm represent less than 10% of the total pore volume; and the pores with diameters less than 0.3 μm represent less than 10% of the total pore volume.

8. A process as claimed in claim 7 wherein the pores with diameters greater than 10 μm represent at most 8% of the total pore volume; and the pores with diameters less than 0.3 μm represent at most 3% of the total pore volume.

9. A process as claimed in claim 1 wherein the carrier has a median pore diameter of at most 2 μm, a total pore volume in the range of from 0.25 to 0.8 ml/g and a surface area of at most 5 m$^2$/g, a total pore volume in the range of from 0.3 to 0.7 ml/g and a surface area in the range of from 1.3 to 3 m$^2$/g.

10. A process as claimed in claim 1 wherein the carrier has a total pore volume of at most 0.6 ml/g.

11. A process as claimed in claim 1 wherein the carrier comprises at least 95 weight percent α-alumina and the carrier has a median pore diameter in the range of from 0.9 to 1.8 μm, a water absorption in the range of from 0.3 to 0.7 g/g and a surface area in the range of from 1.4 m$^2$/g to 2.5 m$^2$/g.

12. A process as claimed in claim 1 wherein the carrier has a water absorption of at most 0.6 g/g.

13. A process as claimed in claim 1 wherein silver is deposited on the carrier in a quantity of from 10 to 500 g/kg, relative to the weight of the catalyst.

14. A process as claimed in claim 1 wherein the carrier comprises alumina and a bond material.

15. A process as claimed in claim 14 wherein the carrier has an α-alumina content of at least 95 weight percent, and wherein the bond material comprises an alkaline earth metal silicate bond material.

16. A process as claimed in claim 15 wherein the bond material further comprises one or more additional components selected from the group consisting of a hydrated alumina, a zirconium component and a titanium component.

17. A process as claimed in claim 1 which comprises, deposited on the carrier in addition to silver, one or more further elements selected from the group consisting of nitrogen, sulfur, phosphorus, boron, fluorine, Group IA metals, Group IIA metals, rhenium, molybdenum, tungsten, chromium, titanium, hafnium, zirconium, vanadium, manganese, thallium, thorium, tantalum, niobium, gallium and germanium and mixtures thereof.

18. A process as claimed in claim 17 wherein the Group IA metals are selected from the group consisting of lithium, potassium, rubidium and cesium.

19. A process as claimed in claim 1 which comprises, deposited on the carrier in addition to silver, one or more of rhenium, molybdenum, tungsten, Group IA metals, and nitrate- or nitrite-forming compounds.

20. A process as claimed in claim 1 which comprises rhenium deposited on the carrier in addition to silver, and optionally a rhenium co-promoter selected from the group consisting of sulfur, phosphorus, boron, and compounds thereof.

21. A process as claimed in claim 1 wherein the carrier has a pore size distribution such that at least 75%, the pore volume contained in pores with diameters in the range of from 0.1 to 10 μm is contained in pores with diameters in the range of from 0.4 to 10 μm.

22. A process as claimed in claim 1 wherein the carrier has a pore size distribution such that the pores with diameters in the range of from 0.1 to 10 μm represent more than 90% of the total pore volume and at least 15% of the pore volume contained in pores with diameters in the range of from 0.1 to 10 μm is contained in pores with diameters in the range of from 5 to 10 μm.

23. A process as claimed in claim 1 wherein the carrier is in the form of formed bodies fired at a temperature of at least 1250° C.

24. A process for the epoxidation of an olefin, which process comprises reacting a feed comprising an olefin and oxygen in the presence of a catalyst comprising a carrier and silver deposited on the carrier, which carrier comprises a bond material and at least 85 weight percent α-alumina, and has a surface area of at least 1 m$^2$/g, a median pore diameter of more than 0.8 μm, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

25. A process as claimed in claim 24 wherein the surface area is at least 1.3 m$^2$/g.

26. A process for the epoxidation of an olefin, which process comprises reacting a feed comprising an olefin and oxygen in the presence of a catalyst comprising a carrier and silver deposited on the carrier, which carrier is in the form of formed bodies fired at a temperature of at least 1250° C. comprising at least 85 weight percent α-alumina, and has a surface area of at least 1 m$^2$/g, a median pore diameter of more than 0.8 μm, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

27. A process for the epoxidation of an olefin, which process comprises reacting a feed comprising an olefin and oxygen in the presence of a catalyst comprising a carrier and silver deposited on the carrier, which carrier comprises at least 85 weight percent α-alumina and has a non-platelet morphology, a surface area of at least 1 m$^2$/g, a median pore diameter of more than 0.8 μm, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

28. A process for the epoxidation of an olefin, which process comprises reacting a feed comprising an olefin and oxygen in the presence of a catalyst comprising a carrier and silver deposited on the carrier, which carrier has a surface area of at least 1 m$^2$/g, a water absorption of at most 0.6 g/g, a median pore diameter of more than 0.8 μm, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

\* \* \* \* \*